United States Patent
Hsu et al.

(10) Patent No.: US 9,827,288 B2
(45) Date of Patent: Nov. 28, 2017

(54) METHOD FOR TREATING A REFRACTORY OR RELAPSED LUNG CANCER

(71) Applicant: MYCOMAGIC BIOTECHNOLOGY CO., LTD., New Taipei (TW)

(72) Inventors: Hsien-Yeh Hsu, Taipei (TW); Tung-Yi Lin, Tainan (TW)

(73) Assignee: MYCOMAGIC BIOTECHNOLOGY CO., LTD., New Taipei (TW)

( * ) Notice: Subject to any disclaimer, the term of this patent is extended or adjusted under 35 U.S.C. 154(b) by 0 days.

(21) Appl. No.: 14/859,839

(22) Filed: Sep. 21, 2015

(65) Prior Publication Data

US 2017/0080048 A1    Mar. 23, 2017

(51) Int. Cl.
*A61K 38/16* (2006.01)
*A61K 9/00* (2006.01)

(52) U.S. Cl.
CPC ............ *A61K 38/16* (2013.01); *A61K 9/0019* (2013.01); *A61K 38/168* (2013.01)

(58) Field of Classification Search
CPC ...... A61K 38/16; A61K 38/168; C07K 14/00; C07K 14/37; C07K 14/415
See application file for complete search history.

(56) References Cited

U.S. PATENT DOCUMENTS

| 7,601,808 B2 | 10/2009 | Lin |
| 2010/0009915 A1 | 1/2010 | Ko et al. |
| 2016/0184389 A1* | 6/2016 | Yu .......................... A61K 38/16 424/185.1 |

FOREIGN PATENT DOCUMENTS

| TW | 201347767 A | * | 12/2013 |
| WO | WO-2014/140648 A1 | * | 9/2014 |
| WO | WO 2015/135483 A1 | * | 9/2015 |

OTHER PUBLICATIONS

Chiu et al. Immunomodulatory Protein from Ganoderma microsporum . . . in Multidrug Resistant Lung Cancer Cells. PLoS One. May 6, 2015, 10(5):e0125774, pp. 1-23.*
Lin et al. A new immunomodulatory protein from Ganoderma microsporum inhibits epidermal growth factor mediated migration and invasion in A549 lung cancer cells. Process Biochemistry. 2010, vol. 45, pp. 1537-1542.*
Bak et al. Physicochemical and Formulation Developability Assessment for Therapeutic Peptide Delivery—A Primer. The AAPS Journal. Jan. 2015, vol. 17, No. 1, pp. 144-155.*
Jinn et al., Functional Expression of FIP-gts, a Fungal Immunomodulatory Protein from Ganoderma Tsugae in Sf21 Insect Cells, Biosci Biotechnol Biochem, 2006, 70, 2627-2.
Boh et al., Ganoderma lucidum and its pharmaceutically active compounds,Biotechnology Annual Review, 2007, 13, 265-301.
Hsu et al., Fip-vvo, a new fungal immunomodulatory protein isolated from Volvariella volvacea, Biochem J, 1997, 323, 557-565.
Ko et al., A new fungal immunomodulatory protein, FIP-fve isolated from the edible mushroom, Flammulina velutipes and its complete amino acid sequence, Eur J Biochem, 1995, 228, 244-249.
Xuanwei et al., Identification of Medicinal Ganoderma Species Based on PCR with Specific Primers and PCR-RFLP, Planta Med, 2008, 74, 197-200.
Liao et al., Transcriptionally Mediated Inhibition of Telomerase of Fungal Immunomodulatory Protein From Ganoderma tsugae in A549 Human Lung Adenocarcinoma Cell Line, Molecular Carcinogenesis 45:220-229.
Liao et al., Induction of premature senescence in human lung cancer by fungal immunomodulatory protein from Ganoderma tsugae, 2008, Food and Chemical Toxicology 46 (2008) 1851-1859.

* cited by examiner

*Primary Examiner* — Jeffrey E. Russel
(74) *Attorney, Agent, or Firm* — WPAT, P.C., Intellectual Property Attorneys; Anthony King; Kay Yang

(57) ABSTRACT

The present invention relates to a method for treating a refractory or relapsed lung cancer. Particularly, the invention provides a method and a formulation of using an immunomodulatory protein derived from *Ganoderma microsporum* in the treatment of a refractory or relapsed lung cancer.

12 Claims, 6 Drawing Sheets
(3 of 6 Drawing Sheet(s) Filed in Color)

A

B

C

METHOD FOR TREATING A REFRACTORY OR RELAPSED LUNG CANCER

FIELD OF THE INVENTION

The present invention relates to a method for treating a refractory or relapsed lung cancer. Particularly, the invention provides a method and a formulation of using an immunomodulatory protein derived from Ganoderma microsporum in the treatment of a refractory or relapsed lung cancer.

BACKGROUND OF THE INVENTION

Lingzhi an herbal mushroom, used in traditional Chinese medicine for at least 2,000 years, which is a species complex that encompasses several fungal species of the genus Ganoderma, most commonly the closely related species Ganoderma lucidum, Ganoderma tsugae, and Ganoderma sichuanense. Many therapeutic effects have been reported of Lingzhi species, such as immunomodulatory, anti-tumor, hepato-protective, antioxidant, and cholesterol-lowering effects (Jinn et al., 2006, Biosci Biotechnol Biochem, 70, 2627-2634). All of these therapeutic effects are attributed from triterpenoids, polysaccharides, and glycoproteins (Boh et al., 2007, Biotechnol Annu Rev, 13, 265-301; Jinn et al., 2006, Biosci Biotechnol Biochem, 70, 2627-2634). A glycoprotein class in Lingzhi named fungal immunomodulatory proteins (FIPs) was recently identified. So far, at least 5 FIPs have been isolated; i.e., LZ-8, (Ganoderma. lucidum), FIP-gts (Ganoderma tsugae), FIP-gja (Ganoderma sinensis) and GMI (Ganoderma microsporum) (Hsu et al., 1997, Biochem J, 323 (Pt 2), 557-565; Ko et al., 1995, Eur J Biochem, 228, 244-249; Xuanwei et al., 2008, Planta Med, 74, 197-200; and U.S. Pat. No. 7,601,808). According to a previous study, FIP-gts from G. tsugae, a popular chemopreventive mushroom in Asia, has anti-cancer function and is involved in the regulation of hTERT/telomerase expression (Liao et al., 2006, Mol Carcinog, 45, 220-229). In addition, FIP-gts inhibits the growth of A549 cancer cells, leading to cell cycle arrest, consequently inducing premature cellular senescence in lung cancer cells. Moreover, FIP-gts results in significant inhibition of tumor growth in athymic nude mice implanted with A549 cells (Liao et al., 2008, Food Chem Toxicol, 46, 1851-1859). US 20100009915 provides a method for suppressing proliferation of a cancer cell and a method for suppressing a tumor cell mobility, comprising providing to the tumor cell a purified polypeptide of a fungal immunomodulatory protein, LZ-8. U.S. Pat. No. 7,601,808 discloses an immunomodulatory protein cloned from Ganoderma microsporum (i.e., GMI) and this protein has immunomodulator efficiency.

Lung cancer, also known as carcinoma of the lung or pulmonary carcinoma, is a malignant lung tumor characterized by uncontrolled cell growth in tissues of the lung. If left untreated, this growth can spread beyond the lung by process of metastasis into nearby tissue or other parts of the body. The main primary types are small-cell lung carcinoma (SCLC) and non-small-cell lung carcinoma (NSCLC).

Small cell lung cancer (SCLC) accounts for approximately 14% of all lung cancers. Combination chemotherapy is currently considered standard first-line therapy for SCLC. The most common regimens include cisplatin or carboplatin and etoposide. Unfortunately, despite the 40-90% response rate to first-line chemotherapy, long-term survival is unusual because patients develop resistance to chemotherapy and relapse. Non-small cell lung cancer (NSCLC) is a heterogeneous aggregate of histologies, including, e.g., epidermoid or squamous carcinoma, adenocarcinoma, and large cell carcinoma. Patients with NSCLC may be divided into three groups that reflect both the extent of the disease and the treatment approach: (1) patients with tumors that are surgically resectable; (2) patients with either locally or regionally advanced lung cancer; and (3) patients with distant metastases at the time of diagnosis. Current treatments for NSCLC include surgery, chemotherapy, and/or radiation therapy. However, current methods of treating NSCLC are often unsatisfactory, and a need exists for effective therapies to treat subjects with NSCLC.

However, there is no therapy to a refractory or relapsed lung cancer and there is a need to develop an agent as treatment means.

SUMMARY OF THE INVENTION

The invention provides a method for treating a refractory or relapsed lung cancer, comprising parenterally administering an effective amount of an immunomodulatory protein derived from Ganoderma or a recombinant thereof (reGMI) as an active agent to a subject suffering from a refractory or relapsed lung cancer. In some embodiments, the immunomodulatory protein or a recombinant thereof is derived from Ganoderma lucidum, Ganoderma tsugae, Ganoderma microsporum or Ganoderma sinensis. In further embodiments, the immunomodulatory protein is LZ-8 derived from Ganoderma lucidum, FIP-gts derived from Ganoderma tsugae, GMI derived from Ganoderma microsporum, or FIP-gja derived from Ganoderma sinensis or a recombinant thereof.

In some embodiments, the refractory or relapsed lung cancer is refractory or relapsed small-cell lung cancer (SCLC), relapsed or refractory non-small cell lung cancer (NSCLC), relapsed or refractory advanced NSCLC, lung squamous carcinoma, lung adenocarcinoma, EGFR-mutated lung cancer, EGFR-overexpressed lung cancer or chemotherapy resistant lung cancer such as gefitinib- or erlotinib-resistant lung cancer. In another some embodiments, the effective amount of the active agent is about 1.5 mg to about 10 mg protein per 70 kg body weight for a human. In some further embodiments, the effective amount of the active agent is about 3.0 mg to about 5 mg protein per 70 kg body weight for a human. In some embodiment, the parenteral route is intravenous, drip, subcutaneous, intraperitoneal or intramuscular injection, or intrathecal or intraventricular administration. In some further embodiments, the method of the invention can further administer a second active agent. The second active agent is used with the immunomodulatory protein sequentially, concurrently or separately.

The present invention also provides an aqueous formulation for parenteral administration comprising an immunomodulatory protein derived from Ganoderma microsporum (GMI) or a recombinant thereof (reGMI) as an active agent. In some embodiment, the amount of the active agent in the injection formulation ranges from about 0.5 mg/ml to about 150 mg/ml.

BRIEF DESCRIPTION OF THE DRAWING

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
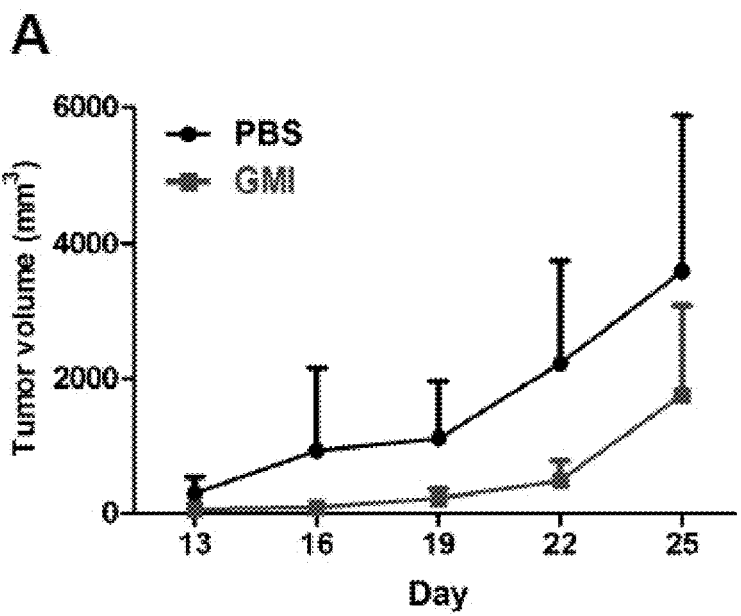
FIG. 1 shows that GMI inhibits the growth of LLC1 allograft mice. (A) The tumor volume was monitored. (B) Representative images of the tumors on the 25th day.
Figure 1:
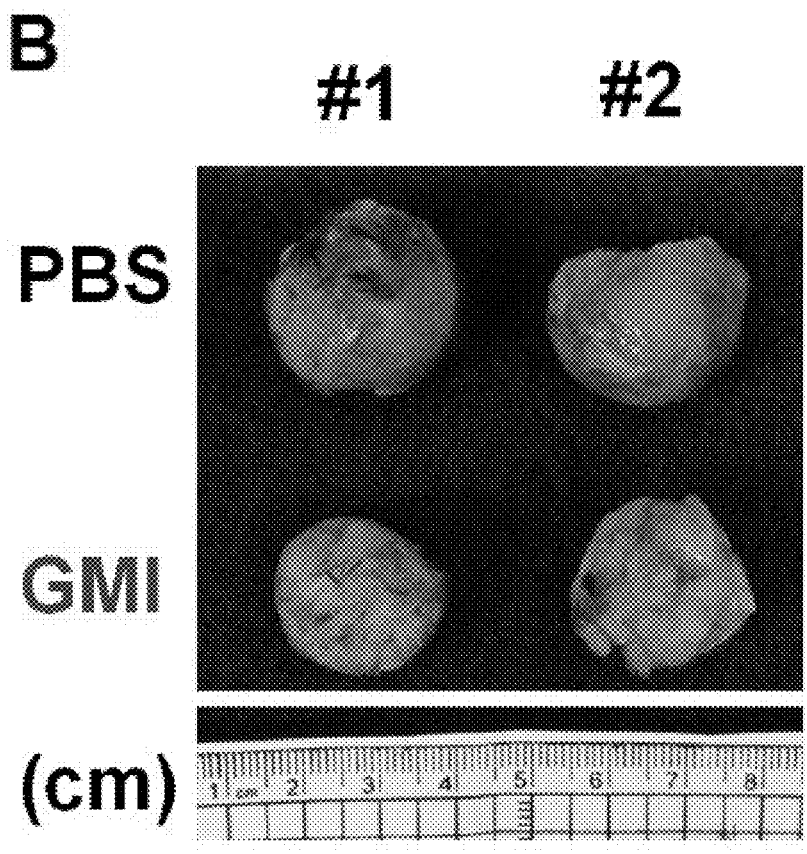

The invention surprisingly found that immunomodulatory protein from *Ganoderma* has an unexpected efficacy in the treatment of a refractory or relapsed lung cancer. The invention also found that the immunomodulatory protein from *Ganoderma* specifically downregulates EGFR protein level via endocytosis and proteasome-mediated degradation which is due to ubiquitination of EGFR.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference.

In this application, the use of the singular includes the plural, the article "a" or "an" means "at least one", and the use of "or" means "and/or", unless specifically stated otherwise.

In this application, the word "comprise," or variations such as "comprises" or "comprising," indicate the inclusion of any recited integer or group of integers but not the exclusion of any other integer or group of integers in the specified method, structure, or composition.

As used herein, the term "therapeutically effective amount" means an amount sufficient to treat a subject afflicted with a disease or to alleviate a symptom or a complication associated with the disease.

As used herein, "treatment" or "treating" or "ameliorating" are used interchangeably herein. These terms refer to an approach for obtaining beneficial or desired results including, but not limited to, therapeutic benefit and/or a prophylactic benefit. Therapeutic benefit pertains to eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. "Treatment" can also mean prolonging survival as compared to expected survival if not receiving treatment. Those in need of treatment include those already with the condition or disorder as well as those prone to have the condition or disorder or those in which the condition or disorder is to be prevented.

As used herein, "refractory cancer" (or "resistant cancer") refers to a cancer not responding to treatment. Some cancer cells have ways of defending themselves against chemotherapy drugs, biological agents and/or radiation therapy. In such cases, the cancer is termed refractory.

As used herein, "relapse" (or "recurrence") means that a cancer had been successfully treated has now returned. The cancer may have returned in its original location, or it may be in a new location.

As used herein, "subject" refers to either a human or non-human animal.

In one aspect, the invention provides a method for treating a refractory or relapsed lung cancer, comprising parenterally administering an effective amount of an immunomodulatory protein derived from *Ganoderma* or a recombinant thereof (reGMI) as an active agent to a subject suffering from a refractory or relapsed lung cancer.

In one embodiment, the immunomodulatory protein or a recombinant thereof is derived from *Ganoderma lucidum, Ganoderma tsugae, Ganoderma microsporum* or *Ganoderma sinensis*. Preferably, the immunomodulatory protein is LZ-8 derived from *Ganoderma lucidum*, FIP-gts derived from *Ganoderma tsugae*, GMI derived from *Ganoderma microsporum*, or FIP-gja derived from *Ganoderma sinensis* or a recombinant thereof. In some embodiments, the immunomodulatory protein derived from *Ganoderma microsporum* (GMI) or *Ganoderma. lucidum* (LZ-8). The sequence of LZ-8 is as follows:
MSDTALIFRLAWDVKKLSFDYTPNWGRGNPNN-FIDTVTTFPKVLTDKAYTYR VAVSGRNL-GVKPSYAVESDGSQKVNFLEYNSGY-GIADTNTIQVFVVDPDTNNDFIIAQW N (SEQ ID NO:5). In one embodiment, the immunomodulatory protein is derived from *Ganoderma microsporum* (GMI) or a recombinant thereof (reGMI). More preferably, the immunomodulatory protein (GMI or reGMI) has the amino acid sequence:
(1) -Leu-Ala-Trp-Asn-Val-Lys-(LAWNVK; SEQ ID NO:1) and (2) -Asp-Leu-Gly-Val-Arg-Pro-Ser-Tyr-Ala-Val-(DL-GVRPSYAV; SEQ ID NO:2), the amino acid sequence of:
MSDTALIFTLAWNVKQLAFDYTPNWGRGRPSSFIDT-VTFPTVLTDKAYTYRVVVSGKD LGVRPSYAVESDG-SQKINFLEYNSGYGIADTNTIQVYVIDPDTGNN-FIVAQWN (SEQ ID NO:3) or the amino acid sequence of EAEAEFMSDTALIFTLAWNVKQLAFDYTPNWGR-GRPSSFIDTVTFPTVLTDKAYTYRVV VSGKDL-GVRPSYAVESDGSQKINFLEYNSGY-GIADTNTIQVYVIDPDTGNNFIVAQWNY LEQKLISEEDLNSAVDHHHHHH (SEQ ID NO:4).

In some embodiments, the refractory or relapsed lung cancer is refractory or relapsed small-cell lung cancer (SCLC), relapsed or refractory non-small cell lung cancer (NSCLC), relapsed or refractory advanced NSCLC, lung squamous carcinoma, lung adenocarcinoma, EGFR-mutated lung cancer, EGFR-overexpressed lung cancer or chemotherapy resistant lung cancer such as gefitinib- or erlotinib-resistant lung cancer.

In some embodiments, the effective amount of the active agent used in the method of the invention is about 10 mg to about 100 mg protein per 70 kg human body weight; preferably, about 20 mg to about 80 mg protein per 70 kg body weight, about 20 mg to about 50 mg protein per 70 kg body weight, about 25 mg to about 50 mg protein per 70 kg body weight, about 30 mg to about 50 mg protein per 70 kg body weight, about 35 mg to about 50 mg protein per 70 kg body weight or about 30 mg to about 40 mg protein per 70 kg body weight.

In another aspect, the invention provides an aqueous formulation for parenteral administration comprising an immunomodulatory protein derived from *Ganoderma microsporum* (GMI) or a recombinant thereof (reGMI) as an active agent. In one embodiment, the amount of the active agent in the injection formulation ranges from about 0.5 mg/ml to about 150 mg/ml; preferably, 1.0 mg/ml to about 100 mg/ml, about 1.0 mg/ml to about 80 mg/ml, about 1.0 mg/ml to about 60 mg/ml, about 1.0 mg/ml to about 40 mg/ml, about 1.0 mg/ml to about 20 mg/ml, about 5 mg/ml to about 150 mg/ml, about 5 mg/ml to about 100 mg/ml, about 10 mg/ml to about 150 mg/ml, or about 10 mg/ml to about 100 mg/ml.

The active agent can be locally or systemically delivered to the subject, and the subject can be a mammal, for example, a human. Administration may be parenteral. Parenteral administration includes intravenous, drip, subcutaneous, intraperitoneal or intramuscular injection, or intrathecal or intraventricular administration.

Parenteral administration of the invention may be employed in parenteral formulations. The parenteral formulations may be in unit dose form in ampoules, small volume parenteral (SVP) vials, large volume parenterals (SVP), pre-filled syringes, small volume infusion or in multi-dose containers. The formulations are suspensions or solutions and may contain formulatory agents such as preserving, wetting, buffering, emulsifying or suspending, stabilizing and/or dispersing agents. Alternatively, the ratio, type, and varieties of the ingredients, active and in-actives, are studied to reach an optimal balance, before use with a suitable vehicle, e.g., sterile, pyrogen-free water. Particular embodiments are contemplated that are substantially free of buffers, stabilizers, and/or preservatives, while still preserve the formulation's chemical stability, pH value, and product sterility.

Parenteral formulations are typically aqueous solutions which may contain excipients such as salts, carbohydrates and buffering agents (preferably at a pH of from 3 to 9.5). Some embodiments have a pH of about 5.5+/−1.0. Additional embodiments are substantially buffer free.

In one embodiment, the parenteral formulations contain a solution of an active agent in an aqueous solvent combined with pH adjusting agents having a pH of about 5.5+/−1.0 and least one isotonicity agent. A water-insoluble inert gas may be carefully bubbled through the solvent to remove oxygen from the medium. Optionally the formulations contain at least one preservative and/or at least one solubility enhancing agent and/or at least one stabilizing agent. In some embodiments, the formulation is substantially free of stabilizing agents and preservatives.

In another embodiment, the method and formulation described herein optionally further comprises a second active agent. The second active agent can be used with the immunomodulatory protein of the invention sequentially, concurrently or separately. In one embodiment, the second active agent include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cisplatin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypernycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflomithineklerriene; emitefur; epirubicin; episteride; erlotinib; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunoruriicin hydrochloride; forfenimex; formestane; fostriecin; fotemustine; gadolinium texaphyrin; gallium nitrate; galocitabine; ganirelix; gefitinib; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; lapatinib; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A plus niyobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone plus pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2, proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; rarnosetran; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonerrnin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; and zinostatin stimalamer. Preferred additional anti-cancer drugs are 5-fluorouracil and leucovorin.

According to the invention, the anti-cancer agent can be a therapeutic antibody, including but not limiting to HERCEPTIN® (Trastuzumab) (Genentech, CA), which is a humanized anti-HER2 monoclonal antibody for the treatment of patients with metastatic breast cancer; REOPRO® (abciximab) (Centocor), which is an anti-glycoprotein IIb/IIIa receptor on the platelets for the prevention of clot formation; ZENAPAX® (daclizumab) (Roche Pharmaceuticals, Switzerland), which is an immunosuppressive, humanized anti-CD25 monoclonal antibody for the prevention of acute renal allograft rejection; PANOREX®, which is a murine anti-17-IA cell surface antigen IgG2a antibody (Glaxo Wellcome/Centocor); BEC2, which is a murine anti-idiotype (GD3 epitope) IgG antibody (ImClone System); IMC-C225, which is a chimeric anti-EGFR IgG antibody (ImClone System); VITAXIN®, which is a humanized anti-.alpha.V.beta.3 integrin antibody (Applied Molecular Evolution/MedImmune); Campath 1H/LDP-03 which is a humanized anti CD52 IgG1 antibody (Leukosite); Smart M195, which is a humanized anti-CD33 IgG antibody (Protein Design Lab/Kanebo); RITUXAN®, which is a chimeric anti-CD20 IgG1 antibody (IDEC Pharm/Genentech, Roche/Zettyaku); LYMPHOCIDE®, which is a humanized anti-CD22 IgG antibody (Immunomedics); LYMPHOCIDE® Y-90 (Immunomedics); Lympho scan (Tc-99m-labeled; radioimaging; Immunomedics); Nuvion (against CD3; Protein Design Labs); CM3, which is a humanized anti-ICAM3 antibody (ICOS Pharm); IDEC-114, which is a primatied primatized anti-CD80 antibody (IDEC Pharm/Mitsubishi); ZEVALIN®, which is a radiolabelled murine anti-CD20 antibody (IDEC/Schering AG); IDEC-131, which is a humanized anti-CD40L antibody (IDEC/Eisai); IDEC-151, which is a primatized anti-CD4 antibody (IDEC); IDEC-152, which is a primatized anti-CD23 antibody (IDEC/Seikagaku); SMART anti-CD3, which is a humanized anti-CD3 IgG (Protein Design Lab); 5G1.1, which is a humanized anti-complement factor 5 (C5) antibody (Alexion Pharm); D2E7, which is a humanized anti-TNF-alpha antibody (CAT/BASF); CDP870, which is a humanized anti-TNF-alpha Fab fragment (Celltech); IDEC-151, which is a primatized anti-CD4 IgG1 antibody (IDEC Pharm/SmithKline Beecham); MDX-CD4, which is a human anti-CD4 IgG antibody (Medarex(Eisai/Genmab); CD20-sreptdavidin (+biotin-yttrium 90; NeoRx); CDP571, which is a humanized anti-TNF-alpha IgG4 antibody (Celltech); LDP-02, which is a humanized anti-alpha-4-beta-7 antibody (LeukoSite/Genentech); OrthoClone OKT4A, which is a humanized anti-CD4 IgG antibody (Ortho Biotech); ANTOVA®, which is a humanized anti-CD40L IgG antibody (Biogen); ANTEGREN®, which is a humanized anti-VLA-4 IgG antibody (Elan); and CAT-152, which is a human anti-TGF-beta 2 antibody (Cambridge Ab Tech).

In a further embodiment, the anti-cancer agent can be selected from the group consisting of cisplatin, gefitinib, lapatinib and erlotinib.

In some embodiments, the parenteral formulation comprises a single dose pH adjusted (about pH 5.5+/−1.0) solution having an effective amount of active agent for treating a cancer; a tonicity agent for adjusting osmolality to about physiological osmolality; optional pH adjusting reagents; and sterile water for injection.

Tonicity agents are sometimes present. The term "tonicity agent" refers to a pharmaceutically acceptable excipient that makes the solution compatible with blood. Suitable tonicity agents include glycerin, lactose, mannitol, dextrose, sodium chloride, sodium sulfate, sorbitol and the like. Preferred tonicity agents include mannitol, sorbitol, lactose and sodium chloride and combinations thereof, and most particularly, sodium chloride. The tonicity agent is added to the injectable to achieve substantially physiological osmolality for injection.

Hypertonic and hypotonic solutions both present complications and undesirable effects when injected. The parenteral formulations described herein are isotonic to minimize or avoid such effects. Since osmolality is the measure of particles in a solution, every component added to the injectable affects the osmolality, thus, adjusting to a final osmolality is complicated, particularly when also adjusting the pH, as addition of the tonicity agent may affect pH and addition of the pH adjusting reagents will affect tonicity.

Optional pH adjusting reagents include acids and bases, such as but not limited to dilute HCl and NaOH. An acid may be added to lower the pH, while the base is added to raise pH. In some instances one or both an acid and a base may be used. In some embodiments, the pH adjusting reagents are chosen to complement the tonicity agent to provide similar ions when in solution. For example, when NaCl is used as a tonicity agent, HCl and/or NaOH may be used as the pH adjusting reagents.

Sterile water for injection is used to increase the volume of the injectable to the desired level.

The tonicity agent, such as NaCl, is employed to achieve an isotonic solution. Isotonic solutions for injection have an osmolality roughly equivalent to physiological osmalality. Other concentrations of NaCl resulted in either undesirable hypertonic or hypotonic solutions.

Additional components, such as active agents, excipients, diluents, buffers, preservatives, etc. may be employed, so long as the parenteral formulation remains isotonic and stable. Any suitable additional active agent could optionally be incorporated into the parenteral formulation.

The present invention is further illustrated by the following Examples, which in no way should be construed as further limiting.

EXAMPLE

Example 1 Efficacy of GMI Formulation for Injection in Treatment of Tumor in LLC Allograft Mice The recombinant immunomodulatory protein derived from *Ganoderma microsporum* (hereafter referred to as "recomGMI") was manufactured by Mycomagic Biotechnology Co., Ltd., according to the method described in U.S. Pat. No. 7,601,808 and has an amino acid sequence shown in FIG. 3B of U.S. Pat. No. 7,601,808. The expression plasmid of LZ-8 gene and the purification of his-tagged rLZ-8 protein were produced as described in Hsu H Y et al., J Cell Physiol. 2008; 215:15-26. Lewis lung carcinoma cell line (LLC1) was purchased from the Bioresource Collection and Research Center (BCRC, Hsinchu, Taiwan).

Male C57BL/6 (6-8 weeks of age) mice were subcutaneously inoculated with LLC1 cells and randomly divided into two groups. Seven days after implantation, the mice were treated with GMI (5 mg/kg) via i.p. injections at intervals of 4 days. The control group received an equal volume of sterile PBS. LLC1 cell is gefitinib resistant cell line, so the study shows that the GMI is potent in inhibiting or treating a refractory or relapsed lung cancer.

The mice will be weighed and randomly distributed across the different experimental groups (n=5). At day 0, approximately $2 \times 10^5$ lung cancer cells suspended in 100 µl serum free DMEM will be subcutaneously (s.c.) implanted into the right flank of all mice for easy observed detection. The mice were sacrificed on the $25^{th}$ day and the tumors were then excised. GMI significantly decreases tumor volume in the LLC1-bearing mice. Tumor size was measured (FIG. 1A) for each mouse using a set of digital calipers at 4 days, and the tumor volume was calculated by the formula L1×L2×H, where L1 is long diameter, L2 is the short diameter and H is the height of the tumor. Representative images of the tumors on the $25^{th}$ day (FIG. 1B).

Figure 2:
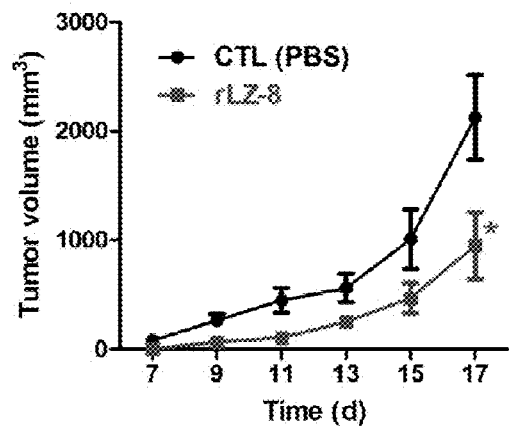
FIG. 2 shows LZ-8 inhibits the tumor growth of LLC1-allograft mice in vivo. (A) The tumor volume was monitored. (B) Representative images of the tumors on the 18th day. (C) The points represent the tumor weight (g) for individual mice exposed to either rLZ-8 or PBS (control) during tumor growth.
Figure 2:
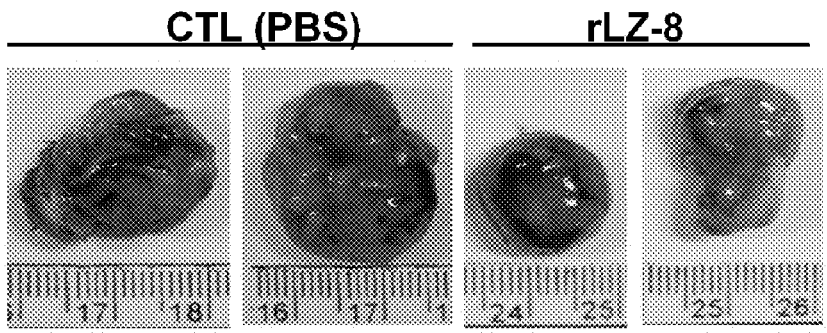
Figure 2:
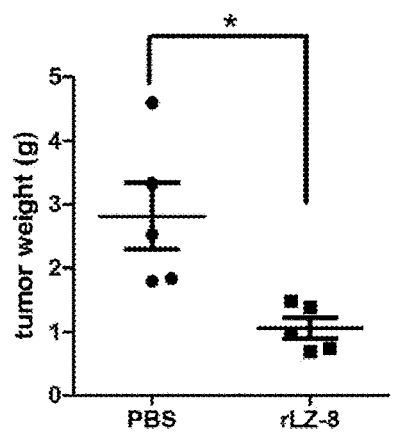

We further examined the effect of rLZ-8 on mice with LLC1-allograft in vivo. LLC1 cells were subcutaneously injected into male C57BL6 mice, and the tumor growth rate was assessed over 17 days. We found that rLZ-8 (7.5 mg/kg) significantly decreases tumor volume in the LLC1-bearing mice (FIGS. 2A and 2B) and tumor weight (FIG. 2C).

Example 2 Cell Viability Assay

Figure 3:
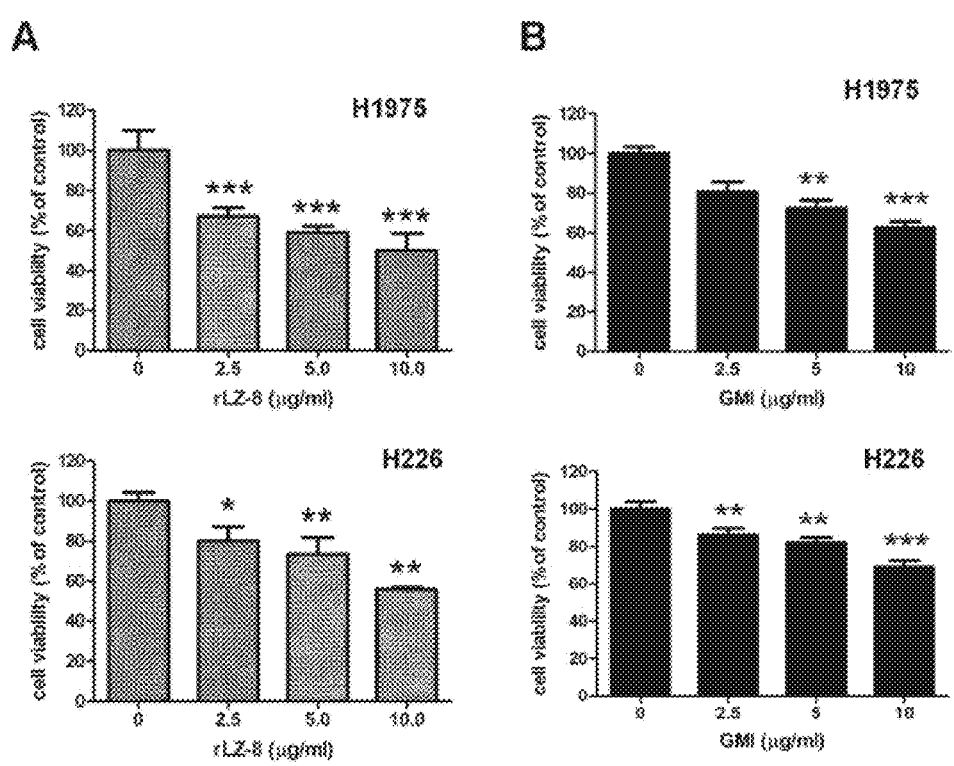
FIGS. 3A and 3B shows the viability of the lung cancer cells was determined using the MTT assay. The lung cancer cells were treated with various doses of GMI (0-10 μg/ml) for 24, 48 or 72 h of indicated cancer cells. The lung adenocarcinoma cell used in the assay is H1975 (72 h), and the squamous carcinoma cell used in the assay is H226 (24 h).

For the 3-(4,5-dimethylthiazole-2-yl)-2,5-diphenyl tetrazolium bromide (MTT) assay, human H1975 and H226 lung cancer cells were seeded in triplicate on a 96-well plate and incubated overnight prior to treating with various concentration of rLZ-8 and GMI (0-20 µg/ml) for 72 h. After incubation, MTT dye was added and the mixture was incubated for 3 h as previous described in Wu C T et al., Carcinogenesis. 2011; 32:1890-6. The cell viabilities (% of control) of rLZ-8 and GMI are shown in FIG. 3.

Example 3 LZ-8 and GMI Bind to EGFR and Induce EGFR Degradation

Figure 4:
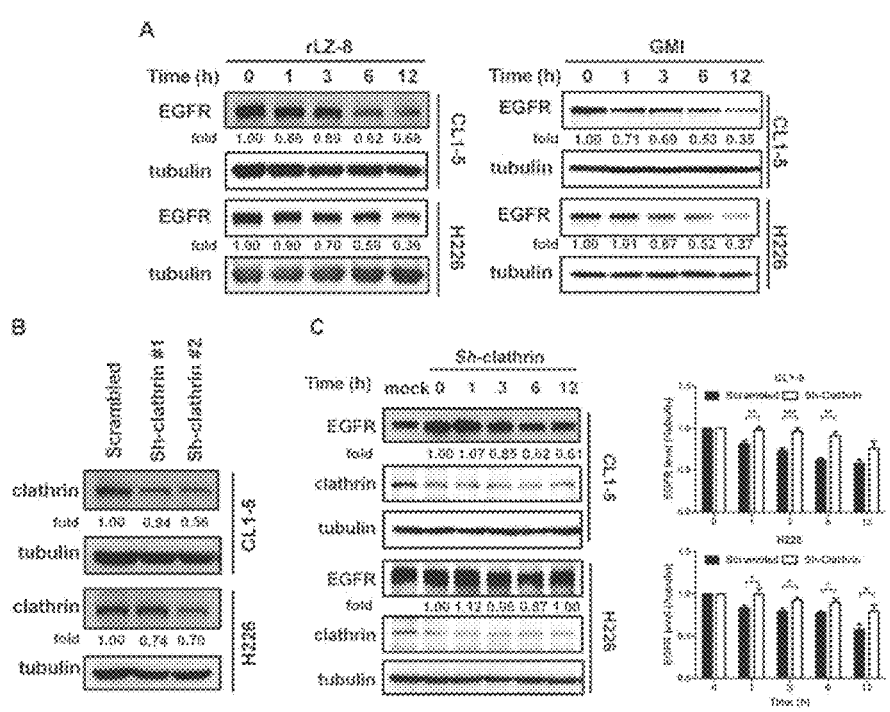
FIG. 4 shows that LZ-8 and GMI physically associate with EGFR and induce EGFR degradation. (A) rLZ-8 and GMI significantly suppressed the EGFR protein levels by western blotting. (B) Clathrin knockdown leads to a reduction in the overall protein levels of clathrin in CL1-5 and H226 cells. (C) Clathrin-knockdown leads to significantly decrease the turnover rate of rLZ-8-induced EGFR degradation in NSCLC cells. Comparing to scrambled and clathrin knockdown cells, clathrin knockdown restored about 42, 18 and 22% of all EGFR degradation events in CL1-5 and H226 cells after rLZ-8 treatment for 12 h, respectively. (D) The co-localization of rLZ-8/GMI and EGFR were determined by fluorescence microscopy. (E) Immunoprecipitation assay was performed by anti-EGFR and anti-his-tag (for detecting rLZ-8) antibody.
Figure 4:
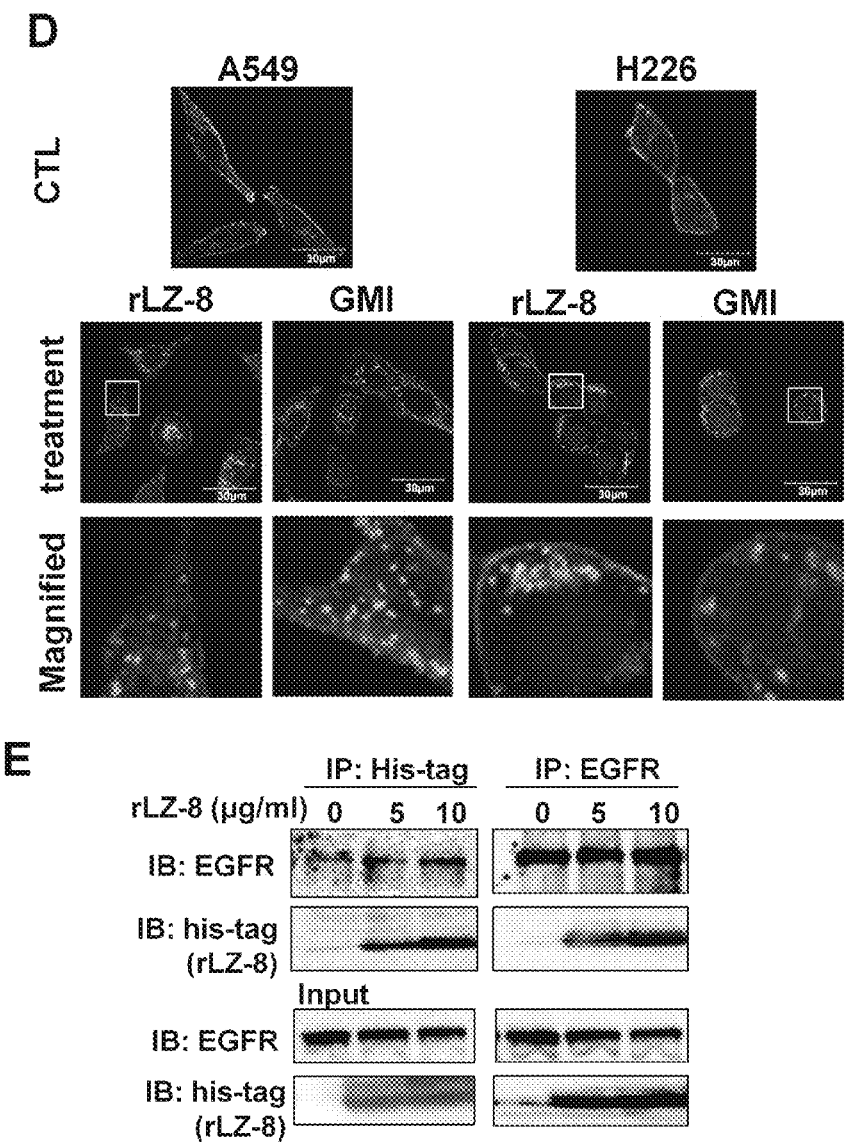

CL1-5 and H226 cells were incubated with rLZ-8 and GMI (5 µg/ml for CL1-5 and 10 µg/ml for H226) for 0-12 h followed by western blotting to detect expression of EGFR. As shown in FIG. 4A, rLZ-8 and GMI significantly suppressed the EGFR protein levels. The regulatory mechanisms of ligand-induced EGFR degradation dependent on endocytosis (Hicke L., FASEB J. 1997; 11:1215-26.). To investigate whether rLZ-8-induced EGFR degradation by inducing endocytosis, we performed depletion of clathrin heavy chain experiments in NSCLC cells. Using clathrin heavy chain shRNAs such as #2755 (sh-S1), #2757 (sh-S2) and #7981 (sh-S3), we confirm the efficacy of clathrin shRNAs, and we found (via Western blot analysis) that clathrin knockdown leads to a reduction in the overall protein levels of clathrin in CL1-5 and H226 cells (FIG. 4B). Next, we examined whether the rLZ-8-induced EGFR degradation dependent on clathrin-mediated endocytosis in NSCLC cells. We found that clathrin-knockdown lead to significantly decrease the turnover rate of rLZ-8-induced EGFR degradation in NSCLC cells (FIG. 4C). Next, comparing to scrambled and clathrin knockdown cells, we found that clathrin knockdown restored about 42, 18 and 22% of all EGFR degradation events in CL1-5 and H226 cells after rLZ-8 treatment for 12 h, respectively (FIG. 4C). These results suggest that a clathrin-mediated endocytosis pathway is involved in the rLZ-8-induced degradation of the EGFR proteins.

Science the downregulation of EGFR by rLZ-8 and GMI may involve an intracellular pathway similar to that induced by EGF-mediated EGFR endocytosis and degradation, we hypothesized that rLZ-8 and GMI could interact with EGFR.

The co-locolization of rLZ-8/GMI and EGFR were determined by fluorescence microscopy. We found that EGFR and rLZ-8 were mainly co-localized on the plasma membrane and formed the punctuate intracellular clusters in the cytoplasm of H226 cells (FIG. 4D). Moreover, we showed the similar results of GMI treatment (FIG. 4D). To further examine the association of rLZ-8 and EGFR, immunoprecipitation assay was performed by anti-EGFR and anti-his-tag (for detecting rLZ-8) antibody. After treatment of rLZ-8 in A549, rLZ-8 was found to be present in the immunoprecipitants obtained by the anti-EGFR antibody, and EGFR was present in the immunoprecipitants retrieved by an anti-his-tag antibody (FIG. 4E). These data suggested that rLZ-8 and GMI are physically associated with EGFR and trigger the EGFR degradation.

Example 4 LZ-8 and GMI Induce Apoptosis in H1975 Cells

Figure 5:
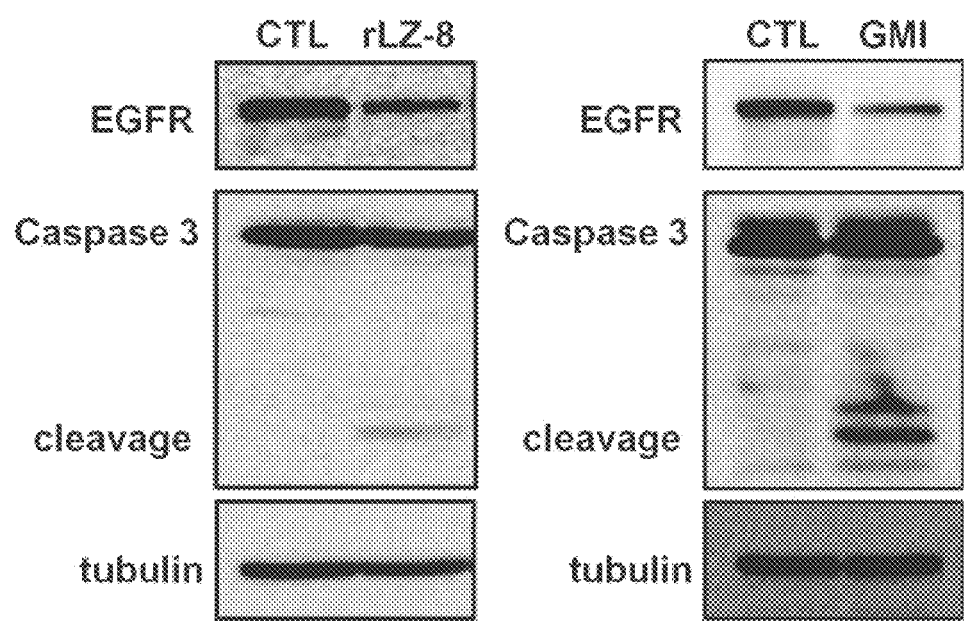
FIG. 5 shows that rLZ-8 and GMI induce downregulation of EGFR level and expression of cleavage caspase 3 in H1975 cells by western blot assay.

Knocking down of EGFR by EGFR siRNA activated activity of caspase3/7, resulting in apoptosis in gefitinib-resistant H1975 cells (Chen G et al., BMC Med. 2012; 10:28). To investigate the apoptosis, human H1975 cells were seed in 60-mm plat-dish and incubated with rLZ-8 (5 µg/ml) and GMI (10 µg/ml) for 48 hours and 72 hours, respectively. Using western blot assay, rLZ-8 and GMI induced downregulation of EGFR level and expression of cleavage caspase 3 in H1975 cells (FIG. 5), suggesting rLZ-8/GMI-induced downregulation of EGFR promotes apoptosis.

What is claimed is:

1. A method for treating a refractory or relapsed lung cancer, comprising parenterally administering an effective amount of an immunomodulatory protein of *Ganoderma* or a recombinant thereof in an aqueous solvent having a pH of about 5.5+/−1.0 to a subject suffering from a refractory or relapsed lung cancer, wherein the refractory or relapsed lung cancer is gefitinib- or erlotinib-resistant lung cancer.

2. The method of claim 1, wherein the *Ganoderma* is *Ganoderma lucidum*, *Ganoderma tsugae*, *Ganoderma microsporum* or *Ganoderma sinensis*.

3. The method of claim 1, wherein the immunomodulatory protein is LZ-8, FIP-gts, GMI, FIP-gja, a recombinant LZ-8, a recombinant FIP-gts, a recombinant GMI or a recombinant FIP-gja.

4. The method of claim 1, wherein the *Ganoderma* is *Ganoderma microsporum*.

5. The method of claim 1, wherein the immunomodulatory protein of *Ganoderma* or a recombinant thereof comprises the amino acid sequence selected from the group consisting of (1) -Leu-Ala-Trp-Asn-Val-Lys-(LAWNVK; SEQ ID NO:1), (2) -Asp-Leu-Gly-Val-Arg-Pro-Ser-Tyr-Ala-Val-(DLGVRPSYAV; SEQ ID NO:2), (3) the amino acid sequence of:

```
                                                (SEQ ID NO: 3)
MSDTALIFTLAWNVKQLAFDYTPNWGRGRPSSFIDTVTFPTVLTDKAYTY

RVVVSGKDLGVRPSYAVESDGSQKINFLEYNSGYGIADTNTIQVYVIDPD

TGNNFIVAQWN
``` and (4) the amino acid sequence of

```
                                                (SEQ ID NO: 4)
EAEAEFMSDTALIFTLAWNVKQLAFDYTPNWGRGRPSSFIDTVTFPTVLT

DKAYTYRVVVSGKDLGVRPSYAVESDGSQKINFLEYNSGYGIADTNTIQV

YVIDPDTGNNFIVAQWNYLEQKLISEEDLNSAVDHHHHHH.
```

6. The method of claim 1, wherein the refractory or relapsed lung cancer is refractory or relapsed small-cell lung cancer (SCLC), relapsed or refractory non-small cell lung cancer (NSCLC), relapsed or refractory advanced NSCLC, lung squamous carcinoma, lung adenocarcinoma, EGFR-mutated lung cancer, or EGFR-overexpressed lung cancer.

7. The method of claim 1, wherein the effective amount of the active agent is about 15 mg to about 100 mg protein per 70 kg body weight for a human.

8. The method of claim 1, wherein the effective amount of the active agent is about 30 mg to about 50 mg protein per 70 kg body weight for a human.

9. The method of claim 1, wherein the parenteral route is intravenous, drip, subcutaneous, intraperitoneal or intramuscular injection, or intrathecal or intraventricular administration.

10. The method of claim 1, further comprising administering a second active agent.

11. The method of claim 10, wherein the second active agent is used with the immunomodulatory protein sequentially, concurrently or separately.

12. The method of claim 1, wherein the treatment with the immunomodulatory protein involves downregulating EGFR protein level via endocytosis and proteasome-mediated degradation which is due to ubiquitination of EGFR.

\* \* \* \* \*

SEQUENCE LISTING

```
<160> NUMBER OF SEQ ID NOS: 5

<210> SEQ ID NO 1
<211> LENGTH: 6
<212> TYPE: PRT
<213> ORGANISM: Ganoderma microsporum

<400> SEQUENCE: 1

Leu Ala Trp Asn Val Lys
1               5

<210> SEQ ID NO 2
<211> LENGTH: 10
<212> TYPE: PRT
<213> ORGANISM: Ganoderma microsporum

<400> SEQUENCE: 2

Asp Leu Gly Val Arg Pro Ser Tyr Ala Val
1               5                   10

<210> SEQ ID NO 3
<211> LENGTH: 111
<212> TYPE: PRT
<213> ORGANISM: Ganoderma microsporum

<400> SEQUENCE: 3

Met Ser Asp Thr Ala Leu Ile Phe Thr Leu Ala Trp Asn Val Lys Gln
1               5                   10                  15

Leu Ala Phe Asp Tyr Thr Pro Asn Trp Gly Arg Gly Arg Pro Ser Ser
                20                  25                  30

Phe Ile Asp Thr Val Thr Phe Pro Thr Val Leu Thr Asp Lys Ala Tyr
            35                  40                  45

Thr Tyr Arg Val Val Val Ser Gly Lys Asp Leu Gly Val Arg Pro Ser
        50                  55                  60

Tyr Ala Val Glu Ser Asp Gly Ser Gln Lys Ile Asn Phe Leu Glu Tyr
65                  70                  75                  80

Asn Ser Gly Tyr Gly Ile Ala Asp Thr Asn Thr Ile Gln Val Tyr Val
                85                  90                  95

Ile Asp Pro Asp Thr Gly Asn Asn Phe Ile Val Ala Gln Trp Asn
            100                 105                 110

<210> SEQ ID NO 4
<211> LENGTH: 140
<212> TYPE: PRT
<213> ORGANISM: Artificial sequence
<220> FEATURE:
```

```
<223> OTHER INFORMATION: Ganoderma microsporum (GMI) or a recombinant
      thereof (reGMI)

<400> SEQUENCE: 4

Glu Ala Glu Ala Glu Phe Met Ser Asp Thr Ala Leu Ile Phe Thr Leu
1               5                   10                  15

Ala Trp Asn Val Lys Gln Leu Ala Phe Asp Tyr Thr Pro Asn Trp Gly
            20                  25                  30

Arg Gly Arg Pro Ser Ser Phe Ile Asp Thr Val Thr Phe Pro Thr Val
        35                  40                  45

Leu Thr Asp Lys Ala Tyr Thr Tyr Arg Val Val Ser Gly Lys Asp
    50                  55                  60

Leu Gly Val Arg Pro Ser Tyr Ala Val Glu Ser Asp Gly Ser Gln Lys
65                  70                  75                  80

Ile Asn Phe Leu Glu Tyr Asn Ser Gly Tyr Gly Ile Ala Asp Thr Asn
                85                  90                  95

Thr Ile Gln Val Tyr Val Ile Asp Pro Asp Thr Gly Asn Asn Phe Ile
                100                 105                 110

Val Ala Gln Trp Asn Tyr Leu Glu Gln Lys Leu Ile Ser Glu Glu Asp
            115                 120                 125

Leu Asn Ser Ala Val Asp His His His His His His
        130                 135                 140

<210> SEQ ID NO 5
<211> LENGTH: 112
<212> TYPE: PRT
<213> ORGANISM: Ganoderma lucidum

<400> SEQUENCE: 5

Met Ser Asp Thr Ala Leu Ile Phe Arg Leu Ala Trp Asp Val Lys Lys
1               5                   10                  15

Leu Ser Phe Asp Tyr Thr Pro Asn Trp Gly Arg Gly Asn Pro Asn Asn
            20                  25                  30

Phe Ile Asp Thr Val Thr Phe Pro Lys Val Leu Thr Asp Lys Ala
        35                  40                  45

Tyr Thr Tyr Arg Val Ala Val Ser Gly Arg Asn Leu Gly Val Lys Pro
    50                  55                  60

Ser Tyr Ala Val Glu Ser Asp Gly Ser Gln Lys Val Asn Phe Leu Glu
65                  70                  75                  80

Tyr Asn Ser Gly Tyr Gly Ile Ala Asp Thr Asn Thr Ile Gln Val Phe
                85                  90                  95

Val Val Asp Pro Asp Thr Asn Asn Asp Phe Ile Ile Ala Gln Trp Asn
            100                 105                 110
```